United States Patent
Begley et al.

(10) Patent No.: US 9,463,194 B2
(45) Date of Patent: Oct. 11, 2016

(54) METHODS OF TREATING PATIENTS CO-INFECTED WITH HIV AND TUBERCULOSIS

(71) Applicant: Gilead Sciences, Inc., Foster City, CA (US)

(72) Inventors: Rebecca Restituto Begley, Palo Alto, CA (US); Joseph Marcello Custodio, San Francisco, CA (US); Brian P. Kearney, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/614,133

(22) Filed: Feb. 4, 2015

(65) Prior Publication Data

US 2015/0216873 A1    Aug. 6, 2015

Related U.S. Application Data

(60) Provisional application No. 61/936,241, filed on Feb. 5, 2014.

(51) Int. Cl.

| | | |
|---|---|---|
| *A61K 31/47* | (2006.01) | |
| *A61K 31/44* | (2006.01) | |
| *A61K 31/535* | (2006.01) | |
| *A61K 31/5377* | (2006.01) | |
| *A61K 45/06* | (2006.01) | |
| *A61K 31/427* | (2006.01) | |
| *A61K 31/438* | (2006.01) | |
| *A61K 31/506* | (2006.01) | |
| *A61K 31/683* | (2006.01) | |
| *A61K 31/675* | (2006.01) | |
| *A61K 31/426* | (2006.01) | |
| *A61K 31/454* | (2006.01) | |
| *A61K 31/473* | (2006.01) | |
| *A61K 31/52* | (2006.01) | |
| *A61K 31/435* | (2006.01) | |

(52) U.S. Cl.
CPC ......... *A61K 31/5377* (2013.01); *A61K 31/426* (2013.01); *A61K 31/427* (2013.01); *A61K 31/435* (2013.01); *A61K 31/438* (2013.01); *A61K 31/454* (2013.01); *A61K 31/47* (2013.01); *A61K 31/473* (2013.01); *A61K 31/506* (2013.01); *A61K 31/52* (2013.01); *A61K 31/675* (2013.01); *A61K 31/683* (2013.01); *A61K 45/06* (2013.01)

(58) Field of Classification Search
CPC ............... A61K 31/47; A61K 31/426; A61K 31/5375; A61K 31/675; A61K 31/683; A61K 31/395
USPC ............... 514/312, 365, 274, 81, 235.5, 278
See application file for complete search history.

(56) References Cited

FOREIGN PATENT DOCUMENTS

| | | |
|---|---|---|
| WO | WO-2009/006199 A1 | 1/2009 |
| WO | WO-2013/115916 A1 | 8/2013 |
| WO | WO-2013/116720 A1 | 8/2013 |
| WO | WO-2014/037121 A1 | 3/2014 |

OTHER PUBLICATIONS

Ramanathan et al. "Pharmacokinetics of emtricitabine, tenofovir, and GS-9137 following coadministration of emtricitabine/tenofovir disoproxil fumarate and ritonacvir-boosted GS-9137," J. Acquir. Immune. Defic. Syndr. 2007, vol. 45, No. 3, pp. 274-279.*
Cohen et al. "Randomized, phase 2 evaluation of two single-tablet regimens elvitegravir/cobicistat/emtricitabine/tenofovir disoproxil fumarate verus efvirenz/emtricitabine/tenofovir disoproxil fumarate for initial treatment of HIV infection," AIDS 2011, vol. 25, No. 6, pp. F7-F12.*
Schutz et al. "Clinical Management of tuberculosis and HIV-1 co-infection," Eur. Respir. J. 2010, vol. 36, pp. 1460-1481.).*
Droste, J.A.H., et al. "Pharmacokinetic Study of Tenofovir Disproxil Fumarate Combined with Rifampin in Healthy Volunteers" *Antimicrobial Agents and Chemotherapy* 49(2), pp. 680-684.
International Search Report and Written Opinion mailed Mar. 20, 2015 for PCT/US2015/014470.
Ramanathan,S. et al. (2012) "Pharmacokinetics and Drug Interaction Profile of Cobicistat Boosted-Elvitegravir with Atzaznavir, Rosuvastatin or Rifabutin" *13th International Workshop on Clinical Pharmacology of HIV Therapy Conference Reports for NATAP*.
van Pinxteren, Laurens et al. (2000) "Control of latent *Mycobacterium tuberculosis* infection is dependent on CD8 T cells" *Eur. J. Immunol.* 30:3689-3698.

* cited by examiner

*Primary Examiner* — Shengjun Wang
(74) *Attorney, Agent, or Firm* — Joel B. Silver

(57) ABSTRACT

The disclosure describes methods for treatment of patients co-infected with HIV and tuberculosis, wherein the patient receives effective amounts of elvitegravir, an antimycobacterial agent and a CYP inhibitor.

13 Claims, No Drawings

METHODS OF TREATING PATIENTS CO-INFECTED WITH HIV AND TUBERCULOSIS

CROSS-REFERENCE TO RELATED APPLICATIONS

This application claims priority to and the benefit under 35 U.S.C. 119(e) of U.S. Provisional Patent Application Ser. No. 61/936,241, filed Feb. 5, 2014, the disclosure of which is hereby incorporated by reference in its entirety.

FIELD

The disclosure describes methods and uses for treatment of patients co-infected with HIV and tuberculosis, wherein the patient receives effective amounts of elvitegravir, an antimycobacterial agent and a CYP inhibitor.

BACKGROUND

The integrase inhibitor elvitegravir (EVG) and pharmacokinetic (PK) enhancer cobicistat (COBI) are components within the single tablet regimen EVG/COBI/emtricitabine (FTC)/tenofovir disoproxil fumarate (TDF) (STRIBILD) for HIV treatment. Rifabutin (RFB) is an antimycobacterial agent used to prevent/treat disseminated mycobacterium avium complex disease and to treat tuberculosis (TB), when combined with other drugs. Previous research identified substantially lower COBI and EVG exposures upon coadministration with RFB. S. Ramanathan, 13$^{th}$ Int'l Workshop on Clinical Pharmacology of HIV Therapy, Barcelona Spain (Apr. 16-18, 2012). As a result, it was determined that "coadmistration of elvitegravir with dose-reduced rifabutin is not recommended." Id.

Because there is a high incidence of patients co-infected with HIV and tuberculosis, a need exists for HIV treatment regimens which can be used in conjunction with tuberculosis treatment regimens.

SUMMARY

The present disclosure provides a method for treating a patient co-infected with human immunodeficiency virus (HIV) and tuberculosis (TB) comprising: administering an integrase inhibitor, an antimycobacterial agent and a cytochrome P450 (CYP) inhibitor to the patient; and achieving a $C_{tau}$ of the integrase inhibitor that exceeds its $IC_{95}$. An embodiment provides an integrase inhibitor, an antimycobacterial agent and a cytochrome P450 (CYP) inhibitor for use in a method of treating a patient co-infected with human immunodeficiency virus (HIV) and tuberculosis (TB), wherein the method comprises administering the integrase inhibitor, the antimycobacterial agent and the cytochrome P450 (CYP) inhibitor to the patient; and achieving a $C_{tau}$ of the integrase inhibitor that exceeds its $IC_{95}$.

One embodiment provides a method for treating a patient co-infected with human immunodeficiency virus (HIV) and tuberculosis (TB) comprising: administering elvitegravir, an antimycobacterial agent and a cytochrome P450 (CYP) inhibitor to the patient; and achieving a $C_{tau}$ of elvitegravir that exceeds its $IC_{95}$. An embodiment provides elvitegravir, an antimycobacterial agent and a cytochrome P450 (CYP) inhibitor for use in a method of treating a patient co-infected with human immunodeficiency virus (HIV) and tuberculosis (TB), wherein the method comprises administering elvitegravir, the antimycobacterial agent and the cytochrome P450 (CYP) inhibitor to the patient; and achieving a $C_{tau}$ of elvitegravir that exceeds its $IC_{95}$.

One embodiment provides the use of a cytochrome P450 (CYP) inhibitor at a daily dose of about 300 mg in combination with elvitegravir and an antimycobacterial agent for treating a patient co-infected with human immunodeficiency virus (HIV) and tuberculosis (TB). Another embodiment provides the use a cytochrome P450 (CYP) inhibitor at a daily dose of about 300 mg in combination with an integrase inhibitor and an antimycobacterial agent for the prevention of HIV and/or TB. One embodiment provides a cytochrome P450 (CYP) inhibitor in combination with elvitegravir and an antimycobacterial agent for use in treating a patient co-infected with human immunodeficiency virus (HIV) and tuberculosis (TB), wherein the CYP inhibitor is administered at a daily dose of about 300 mg. Another embodiment provides a cytochrome P450 (CYP) inhibitor in combination with an integrase inhibitor and an antimycobacterial agent for use in the prevention of HIV and/or TB, wherein the CYP inhibitor is administered at a daily dose of about 300 mg.

One embodiment provides the use of a cytochrome P450 (CYP) inhibitor twice daily (e.g. at a dose of about 150 mg) in combination with an integrase inhibitor and an antimycobacterial agent for treating a patient co-infected with human immunodeficiency virus (HIV) and tuberculosis (TB). Another embodiment provides the use a cytochrome P450 (CYP) inhibitor twice daily (e.g. at a dose of about 150 mg) in combination with an integrase inhibitor and an antimycobacterial agent for the prevention of HIV and/or TB. One embodiment provides cytochrome P450 (CYP) inhibitor in combination with an integrase inhibitor and an antimycobacterial agent for use in treating a patient co-infected with human immunodeficiency virus (HIV) and tuberculosis (TB), wherein the CYP inhibitor is administered twice daily (e.g. at a dose of about 150 mg). Another embodiment provides a cytochrome P450 (CYP) inhibitor in combination with an integrase inhibitor and an antimycobacterial agent for use in the prevention of HIV and/or TB, wherein the CYP inhibitor is administered twice daily (e.g. at a dose of about 150 mg).

One embodiment provides a method for prevention of HIV and/or TB comprising: administering elvitegravir, an antimycobacterial agent and a cytochrome P450 (CYP) inhibitor to the patient; and achieving a $C_{tau}$ of elvitegravir that exceeds its $IC_{95}$. An embodiment provides elvitegravir, an antimycobacterial agent and a cytochrome P450 (CYP) inhibitor for use in a method for the prevention of HIV and/or TB, wherein the method comprises administering elvitegravir, the antimycobacterial agent and the cytochrome P450 (CYP) inhibitor to the patient; and achieving a $C_{tau}$ of elvitegravir that exceeds its $IC_{95}$.

In another embodiment, the integrase inhibitor is elvitegravir, raltegravir or dolutegravir. In another embodiment, the CYP inhibitor is cobicistat. In another embodiment, the CYP inhibitor is ritonavir. In another embodiment, the antimycobacterial agent is rifabutin.

In another embodiment, the integrase inhibitor, such as elvitegravir, is administered to the patient once a day. In another embodiment, the CYP inhibitor is administered to the patient at least twice a day. In another embodiment, the CYP inhibitor is administered to the patient in two different dosages: a first dose which is coadministered with the integrase inhibitor, such as elvitegravir, and a second dose without the integrase inhibitor, such as elvitegravir. In another embodiment, the first dose further comprises emtricitabine and tenofovir disoproxil fumarate or tenofovir alafenamide fumarate. In another embodiment, the first dose is a single tablet regimen comprising the integrase inhibitor, cobicistat, emtricitabine and tenofovir disoproxil fumarate or tenofovir alafenamide fumarate. In another embodiment, the second dose consists essentially of cobicistat.

Another embodiment provides further administration of at least one compound selected from the group consisting of emtricitabine, tenofovir disoproxil fumarate, tenofovir alafenamide fumarate, atazanavir, lopinavir, darunavir, fosamprenavir and tipranavir. In one embodiment, the disclosure provides further administration of at least one compound selected from the group consisting of emtricitabine, tenofovir disoproxil fumarate, and tenofovir alafenamide fumarate.

In another embodiment, rifabutin is administered to the patient once every other day.

Another embodiment provides an inhibitory quotient (IQ) of elvitegravir that is greater than 1, 2, 3, 4, 5, 6, 7, 8, 9 or 10. Another embodiment further comprises achieving a $C_{tau}$ of the integrase inhibitor, such as elvitegravir, that exceeds its $IC_{95}$ by at least 5-fold. Another embodiment further comprises achieving a $C_{tau}$ of the integrase inhibitor, such as elvitegravir, that exceeds its $IC_{95}$ by at least 10-fold.

In another embodiment, the CYP inhibitor is administered to the patient at about 50 mg, about 75 mg, about 100 mg, about 125 mg, about 150 mg, about 175 mg, about 200 mg, about 225 mg, about 250 mg, about 275 mg, or about 300 mg, once, twice or three times a day. In another embodiment, the CYP inhibitor is administered to the patient at about 50 mg to 300 mg, at about 100 mg to 200 mg, or about 125 mg to 175 mg, twice per day. In another embodiment, the CYP inhibitor is administered to the patient at about 150 mg, twice per day.

In another embodiment, rifabutin is administered at about 100 mg, 150 mg, 200 mg, 250 mg, 300 mg, 350 mg, or 400 mg dose to the patient, once a day or once every other day or once every third day. In another embodiment, rifabutin is administered at about 100 mg to 500 mg, or about 200 mg to 400 mg, once a day or once every other day or once every third day. In another embodiment, rifabutin is administered at about 300 mg once every other day.

In another embodiment, elvitegravir is administered to the patient at about 50 mg, about 75 mg, about 100 mg, about 125 mg, about 150 mg dose, about 175 mg, about 200 mg, about 225 mg, about 250 mg, about 275 mg, or about 300 mg, once, twice or three times a day or once every other day. In another embodiment, elvitegravir is administered to the patient at about 50 mg to 300 mg, at about 100 mg to 200 mg, or about 125 mg to 175 mg, once per day. In another embodiment, elvitegravir is administered to the patient at about 150 mg, once per day.

In another embodiment, the antimycobacterial activity of rifabutin is increased from the co-administration of the CYP inhibitor. In another embodiment, the amount of an antimycobacterial metabolite of rifabutin, 25-O-desacetylrifabutin, is increased from the co-administration of the CYP inhibitor.

Another embodiment provides a pharmaceutical composition comprising an integrase inhibitor, rifabutin and a cytochrome P450 (CYP) inhibitor. In another embodiment, the CYP inhibitor is cobicistat. In another embodiment, the CYP inhibitor is ritonavir. In another embodiment, the integrase inhibitor is elvitegravir. In another embodiment, the integrase inhibitor is dolutegravir.

In some embodiments and uses of the invention, cobicistat is administered to the patient at a dose of about 150 mg, twice per day, elvitegravir is administered to the patient at a dose of about 150 mg, once per day, and rifabutin is administered to the patient at a dose of about 150 mg once every other day.

Another embodiment provides a pharmaceutical composition consisting essentially of an integrase inhibitor, rifabutin and a cytochrome P450 (CYP) inhibitor. In another embodiment, the CYP inhibitor is cobicistat. In another embodiment, the CYP inhibitor is ritonavir. In another embodiment, the integrase inhibitor is elvitegravir. In another embodiment, the integrase inhibitor is dolutegravir.

An embodiment provides an integrase inhibitor (e.g. elvitegravir), an antimycobacterial agent (e.g. rifabutin) and a cytochrome P450 (CYP) (e.g. cobicistat) for use in therapy, e.g. in treating a patient co-infected with human immunodeficiency virus (HIV) and tuberculosis (TB), or in preventing HIV and/or TB.

In certain embodiments, "preventing HIV and/or TB" means preventing HIV. In other embodiments, "preventing HIV and/or TB" means preventing TB. In other embodiments, "preventing HIV and/or TB" means preventing TB and HIV.

DETAILED DESCRIPTION

In the treatment of HIV, it is important that concentrations of HIV drugs be high enough to inhibit HIV replication. If this does not happen, HIV can continue to replicate thereby contributing to resistance, resulting in HIV strains that are not responsive to antiretroviral therapy. At such point, higher amounts of HIV drugs, such as protease and integrase inhibitors, are required to inhibit replication, which leads to drug toxicity.

Accordingly, to avoid resistance, drug failure and ultimately drug toxicity, HIV inhibitors should maintain in vivo $C_{troughs}$ ($C_{tau}$) well above their $IC_{95}$ values. HIV inhibitors with Ctroughs below their $IC_{95}$ value results in HIV inhibitor-resistant viruses and patients with virologic failure.

The inhibitory quotient (IQ) is expressed as the actual $C_{trough}$ over that of the in vitro inhibitory concentration of the HIV virus, determined using phenotypic assays (i.e., $IQ=C_{trough}/IC_{95}$). In essence, the IQ or $C_{tau}$ over $IC_{95}$ is a buffer zone between drug concentrations that are active against drug-resistant or wild-type virus and drug concentrations that allow for the emergence of drug-resistance mutants. Consequently, drugs with the lowest IQ are more likely to be associated with poor virologic outcome, whereas those with high IQs are more likely to stay on top of—and maintain control of—viral replication. The dosing regimen provided herein provides an IQ of greater than 10 for elvitegravir.

Rifabutin is an antimycobacterial agent used to prevent/treat disseminated mycobacterium avium complex disease and to treat tuberculosis (when combined with other drugs). Previous research identified substantially lower COBI and EVG exposures upon coadministration with RFB. S. Ramanathan, 13th Int'l Workshop on Clinical Pharmacology of HIV Therapy, Barcelona Spain (Apr. 16-18, 2012). As a result, it was determined that "coadministration of elvitegravir with dose-reduced rifabutin is not recommended." Id.

As described herein, upon co-dosing with cobicistat twice daily (BID), RFB exposures ($AUC_{tau}$ and $C_{max}$) were within the predefined no-effect boundary, while EVG and RFB $C_{tau}$ were modestly higher (59% and 41%, respectively), versus reference treatments. Importantly, EVG $C_{tau}$, the parameter best associated with antiviral activity or failure if too low, was >10-fold above the $IC_{95}$ (45 ng/mL). Additionally, the exposure of 25-O-desacetylrifabutin (RFB metabolite contributing ~10% of total antimycobacterial activity) were markedly higher (~12-fold) following EVG QD (once daily)+COBI BID+RFB QOD (once every other day) versus RFB alone. A total increase in antimycobacterial activity (parent plus metabolite) was less than 2-fold. Accordingly, twice daily administration of COBI with once daily EVG mitigated the effect of RFB induction upon their coadministration, resulting in a $C_{tau}$ of elvitegravir that is many-fold above the $IC_{95}$ of elvitegravir, with an IQ greater than 10.

An "antimycobacterial agent" refers to an agent which treats mycobacterial infections, specifically tuberculosis. Examples include rifabutin (RFB), ethambutol, isoniazid, pyrazinamide, rifampicin, streptomycin, amikacin, kanamycin, capreomycin, viomycin, enviomycin, ciprofloxacin, levofloxacin, moxifloxacin, ethionamide, prothionamide, cycloserine, closerin, terizidone, clarithromycin, linezolid, thioacetazone, thioridazine and R207910.

"$C_{tau}$" or "$C_{trough}$" is a pharmacokinetic (PK) parameter that refers to the concentration of the drug at the end of the dosing interval. This parameter is obtained by direct measurement of the drug concentrations in a plasma sample collected from the study subject at the end of the dosing interval (i.e., 24 hours post-dose) using a validated high-performance liquid chromatography/tandem mass spectrometry (HPLC/MS/MS) bioanalytical assay.

"Cobicistat" refers to 1,3-thiazol-5-ylmethyl (2R,5R)-(5-{[(2S)-2-[(methyl{[2-(propan-2-yl)-1,3-thiazol-4-yl]methyl}carbamoyl)amino]]-4-(morpholin-4-yl)butanamido}-1,6-diphenylhexan-2-yl)carbamate) and has been shown to be a mechanism-based inhibitor of CYP3A enzymes with greater specificity than ritonavir. Xu et al., ACS Med. Chem. Lett. (2010), 1, pp. 209-13.

A "cytochrome P450 inhibitor" or CYP inhibitor refers to a mechanistic based inhibitor of CYP. Examples include cobicistat and ritonavir.

As used herein, the term "co-administer" refers to administration of two or more agents within a 24 hour period of each other, for example, as part of a clinical treatment regimen. In other embodiments, "co-administer" refers to administration of two or more agents within 2 hours of each other. In other embodiments, "co-administer" refers to administration of two or more agents within 30 minutes of each other. In other embodiments, "co-administer" refers to administration of two or more agents within 15 minutes of each other. In other embodiments, "co-administer" refers to administration at the same time, either as part of a single formulation or as multiple formulations that are administered by the same or different routes.

As used herein, "co-infection" is the simultaneous infection of a patient by multiple pathogen species. Co-infection is of particular human health importance because pathogen species can interact within the host yielding a net effect often greater than the individual infections. A globally common co-infection involves tuberculosis and HIV.

"Emtricitabine" or "FTC" refers to (2R,5S,cis)-4-amino-5-fluoro-1-(2-hydroxymethyl-1,3-oxathiolan-5-yl)-(1H)-pyrimidin-2-one. Honde et al., J. Pharm. Res. and Clin. Practice, (2011), 1(4), pp. 51-66.

"$IC_{95}$" or "$EC_{95}$" refers to the inhibitory concentration required to achieve 95% of the maximum desired effect, which in the case of EVG is the inhibition of the HIV virus. This term is obtained using an in vitro assay evaluating the concentration-dependent inhibition of wild type HIV virus.

"IQ" or "inhibitory quotient" refers to the ratio between the trough drug concentration ($C_{tau}$) and level of drug resistance of the HIV isolate as determined by the $IC_{95}$ (i.e. $C_{tau}/IC_{95}$).

"Rifabutin" (RFB) or "Mycobutin" refers to the compound 1',4-didehydro-1-deoxy-1,4-dihydro-5'-(2-methylpropyl)-1-oxorifamycin XIV or (9S,12E,14S,15R,16S,17R,18R,19R,20S,21S,22E,24Z)-6,16,18,20-tetrahydroxy-1'-isobutyl-14-methoxy-7,9,15,17,19,21,25-heptamethyl-spiro[9,4-(epoxypentadeca[1,11,13]trienimino)-2H-furo[2',3':7,8]naphth[1,2-d]imidazole-2,4'-piperidine]-5,10,26-(3H,9H)-trione-16-acetate. Brogden et al., Drugs (1994), vol. 47, 6, pp. 983-1009.

"Ritonavir" refers to the compound 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl] carbamate) and is a CYP inhibitor. Xu et al., ACS Med. Chem. Lett. (2010), 1, 209-13.

"Tenofovir alafenamide" or "TAF" is {9-[(R)-2-[[(S)—[[(S)-1-(isopropoxycarbonyl)ethyl]amino]phenoxyphosphinyl]-methoxy]propyl]adenine}. TAF may be associated with fumarate, such as monofumarate and hemifumarate. See e.g. U.S. Pat. Nos. 7,390,791, 7,803,788, and 8,754,065.

"Tenofovir disoproxil" or "TD" is 9-[(R)-2-[[bis[[(isopropoxycarbonyl)oxy]methoxy]phosphinyl]methoxy]propyl]adenine. TD may be associated with fumarate, such as monofumarate. See e.g. U.S. Pat. Nos. 5,922,695, 5,935, 946, and 5,977,089.

"Therapeutically effective amount" refers to that amount of the compound being administered which will prevent a condition, or will relieve to some extent one or more of the symptoms of the disorder being treated. Pharmaceutical compositions suitable for use herein include compositions wherein the active ingredients are contained in an amount sufficient to achieve the intended purpose. Determination of a therapeutically effective amount is well within the capability of those skilled in the art, especially in light of the detailed disclosure provided herein. As used herein, treatment refers to inhibition, reduction, elimination or alleviation of a disease as well as prevention.

The present invention also provides a method for the treatment or prophylaxis of diseases, disorders, and conditions. An example of a disease, disorder, or condition includes, but is not limited to, a retrovirus infection, or a disease, disorder, or condition associated with a retrovirus infection. Retroviruses are RNA viruses and are generally classified into the alpharetrovirus, betaretrovirus, deltaretrovirus, epsilonretrovirus, gammaretrovirus, lentivirus, and spumavirus families. Examples of retroviruses include, but are not limited to, human immunodeficiency virus (HIV), human T-lymphotropic virus (HTLV), rous sarcoma virus (RSV), and the avian leukosis virus. In general, three genes of the retrovirus genome code for the proteins of the mature virus: gag (group-specific antigen) gene, which codes for the core and structural proteins of the virus; pol (polymerase) gene, which codes for the enzymes of the virus, including reverse transcriptase, protease, and integrase; and env (envelope) gene, which codes for the retrovirus surface proteins.

Retroviruses attach to and invade a host cell by releasing a complex of RNA and the pol products, among other things, into the host cell. The reverse transcriptase then produces double stranded DNA from the viral RNA. The double stranded DNA is imported into the nucleus of the host cell and integrated into the host cell genome by the viral integrase. A nascent virus from the integrated DNA is formed when the integrated viral DNA is converted into mRNA by the host cell polymerase and the proteins necessary for virus formation are produced by the action of the virus protease. The virus particle undergoes budding and is released from the host cell to form a mature virus.

The active agents may be administered to a human in any conventional manner. While it is possible for the active agents to be administered as compounds, they are preferably administered as a pharmaceutical composition. The salt, carrier, or diluent should be acceptable in the sense of being compatible with the other ingredients and not deleterious to the recipient thereof. Examples of carriers or diluents for oral administration include cornstarch, lactose, magnesium stearate, talc, microcrystalline cellulose, stearic acid, povidone, crospovidone, dibasic calcium phosphate, sodium starch glycolate, hydroxypropyl cellulose (e.g., low substituted hydroxypropyl cellulose), hydroxypropylmethyl cellulose (e.g., hydroxypropylmethyl cellulose 2910), and sodium lauryl sulfate.

The pharmaceutical compositions may be prepared by any suitable method, such as those methods well known in the art of pharmacy, for example, methods such as those described in Gennaro et al., Remington's Pharmaceutical Sciences (18th ed., Mack Publishing Co., 1990), especially Part 8: Pharmaceutical Preparations and their Manufacture. Such methods include the step of bringing into association the compounds with the carrier or diluent and optionally one or more accessory ingredients. Such accessory ingredients include those conventional in the art, such as, fillers, binders, excipients, disintegrants, lubricants, colorants, flavoring agents, sweeteners, preservatives (e.g., antimicrobial preservatives), suspending agents, thickening agents, emulsifying agents, and/or wetting agents.

In practice, the amount of each compound (e.g. the compounds described herein) to be administered ranges from about 0.001 to 100 mg per kg of body weight, such total dose being given at one time or in divided doses. Each compound may be administered alone or in combination with one or more other drugs (e.g. the compounds and combinations disclosed herein). Generally, each compound will be administered as a formulation in association with one or more pharmaceutically acceptable excipients. The choice of excipient will to a large extent depend on factors such as the particular mode of administration, the effect of the excipient on solubility and stability, and the nature of the dosage form.

Provided herein is a product comprising an integrase inhibitor, an antimycobacterial agent and a cytochrome P450 (CYP) inhibitor as a combined preparation for simultaneous, separate or sequential use in a method described herein, e.g. a method of treating a patient co-infected with human immunodeficiency virus (HIV) and tuberculosis (TB), or for the prevention of HIV and/or TB.

Pharmaceutical compositions suitable for the delivery of compounds described herein and methods for their preparation will be readily apparent to those skilled in the art. Such compositions and methods for their preparation may be found, for example, in Remington's Pharmaceutical Sciences, 19th Edition (Mack Publishing Company, 1995).

In the following description of the examples, specific embodiments in which the invention may be practiced are described. These embodiments are described in sufficient detail to enable those skilled in the art to practice the invention. Other embodiments may be utilized, and logical and other changes may be made without departing from the scope of the invention. The following detailed description is, therefore, not to be taken in a limiting sense, and the scope of the invention is defined only by the appended claims, along with the full scope of equivalents to which such claims are entitled.

EXAMPLES

Example 1

A Pharmacokinetic Interaction Between Cobicistat Boosted-Elvitegravir in Combination with Rifabutin, Utilizing Twice Daily Administration of Cobicistat to Overcome Rifabutin-Mediated Induction The effects of a second daily dose (PM dosing) of 150 mg Cobicistat (COBI, co), in combination with Rifabutin (RFB; QOD dosing) with the Composition (EVG/COBI); QD, AM dosing) were determined. This study evaluated the steady-state pharmacokinetics and safety of the coadministered Composition and an additional dose of COBI in combination with RFB QOD.

Methods

In this single cohort, open label, fixed sequence study, healthy volunteers were administered study treatments as follows: the Composition (EVG 150 mg and COBI 150 mg) QD for 10 days (treatment 1), the Composition QD, morning dose and COBI (150 mg QD, evening dose) and Rifabutin (150 mg QOD, morning dose) (treatment 2) and then RFB 300 mg QD (treatment 3). Lack of PK alteration bounds for 90% confidence intervals (CI) about the geometric mean ratio (GMR) (coadministration: alone) were 70-143% for EVG and RFB.

Results

All subjects (N=14) completed the study. All treatments were generally well tolerated and no Grade 2, 3, 4, or serious adverse events were observed. The most frequently observed adverse events in the study were not unexpected and were in line with previous studies with these agents and included infections and infestations (~36% RFB+COBI+the Composition), skin and subcutaneous tissue disorders (~21% the Composition), nervous system disorders (~21% RFB+COBI+the Composition) and Renal and urinary disorders (~21% RFB+COBI+the Composition). Pharmacokinetic results were as shown in Table 1:

TABLE 1

| | % GMR (90% CI) | |
|---|---|---|
| | EVG; (n = 14) | RFB (n = 14) |
| $AUC_{tau}$ | 114.79 (107.32, 122.78) | 114.44 (100.27, 130.62) |
| $C_{max}$ | 100.32 (93.42, 107.74) | 116.26 (101.44, 133.23) |
| $C_{tau}$ | 159.08 (134.60, 188.00) | 140.76 (123.76, 160.09) |

Total antimycobacterial activity increased 1.76-fold (90% CI: 1.58, 1.96). The Composition exposures were maintained in the presence of RFB dosing by the second (PM) dose of COBI; in particular the EVG $C_{tau}$ was >10-fold above the $IC_{95}$ (45 ng/mL), via maintenance of COBI-mediated inhibition of CYP3A4 throughout the Composition's dosing interval (24 hrs) as EVG undergoes CYP3A4 metabolism and RFB is a CYP3A4 inducer. Based on these data, twice daily administration of COBI with once daily EVG mitigated the effect of RFB induction upon their coadministration.

The second, evening dose of 150 mg COBI was selected based two different studies, wherein the first study ritonavir exposure was maintained through the end of the dosing interval, corresponding to achieving bioequivalent EVG when co-administered with RFB QOD. In the second study, both EVG and COBI levels were maintained through ~18 hrs, but were 70% lower by 24 hrs post dose when co-administered with RFB. The additional evening dose of COBI was intended to bolster CYP3A inhibition and therefore maintain EVG levels throughout the Composition dosing interval of 24 hrs, with a goal of obtaining an EVG $C_{tau}$>10× the IC95 (45 ng/mL), without significantly affecting overall EVG exposures. As RFB is a CYP3A4 substrate as well, consideration was also given to maintaining clinically acceptable RFB exposures, based on currently approved labeled use of RFB that recommends RFB 150 mg QOD regimen with boosted PI ARV regimens. Thus, the dosing regimen of the Composition (QD, morning dose) plus 150 mg COBI (QD, evening dose) plus RFB (QOD, morning dose) provides clinically equivalent exposures of EVG throughout the 24 hr dosing interval of the Composition as compared with no COBI evening dose, and clinically equivalent exposures of RFB throughout the 48 hr dosing interval as compared with dosing of RFB (300 mg QD) alone.

Following dosing of the Composition plus 150 mg COBI (QD, evening dose) plus RFB (QOD, morning dose), EVG and RFB exposures ($AUC_{tau}$ and $C_{max}$) were within the predefined no-effect boundary (70-143%), while EVG and RFB $C_{tau}$ were modestly higher (59% and 41%, respectively), versus reference treatments. Importantly, EVG $C_{tau}$, the parameter best associated with antiviral activity, was >10-fold above the $IC_{95}$ (45 ng/mL). Consistent with COBI BID dosing, COBI exposures were markedly higher following dosing of the Composition plus 150 mg COBI (QD, evening dose) plus RFB (QOD, morning dose), vs reference treatment. Also, the exposure of 25-O-desacetylrifabutin (CYP3A-metabolized RFB metabolite, contributing ~10% of total antimycobacterial activity) were markedly higher (~12-fold) following dosing of the Composition plus 150 mg COBI (QD, evening dose) plus RFB (QOD, morning dose). However, the total increase in antimycobacterial activity (parent plus metabolite) was less than 2-fold, which is consistent with the change in anti-mycobacterial activity observed upon coadministration with boosted-protease inhibitor regimens. Accordingly, an additional evening dose of 150 mg COBI administered with the Composition in the presence of RFB 150 mg QOD mitigates the effect of RFB induction and maintain clinically equivalent exposures of both the EVG and RFB.

Consequently, an additional evening dose of 150 mg COBI administered with the Composition (EVG/COBI) in the presence of RFB 150 mg QOD maintains clinically equivalent exposures of both EVG and RFB. Twice daily administration of COBI with once daily EVG mitigated the effect of RFB induction upon their co-administration.

The invention claimed is:

1. A method for treating a patient co-infected with human immunodeficiency virus (HIV) and tuberculosis (TB) comprising: administering elvitegravir, rifabutin, and cobicistat to the patient; and achieving a $C_{tau}$ of elvitegravir that exceeds its $IC_{95}$, wherein elvitegravir is administered to the patient once a day; and cobicistat is administered at least twice a day in a first dose which is coadministered with elvitegravir and a second dose without elvitegravir.

2. The method of claim 1, wherein the first dose further comprises emtricitabine and tenofovir disoproxil fumarate or tenofovir alafenamide fumarate.

3. The method of claim 2, wherein the first dose is a single tablet regimen comprising elvitegravir, cobicistat, emtricitabine and tenofovir disoproxil fumarate or tenofovir alafenamide fumarate.

4. The method of claim 3, wherein the second dose consists essentially of cobicistat.

5. The method of claim 1, wherein the rifabutin is administered to the patient once every day.

6. The method of claim 1, wherein the rifabutin is administered to the patient once every other day.

7. The method of claim 1, comprising achieving a $C_{tau}$ of elvitegravir that exceeds its $ICs_{95}$ by at least 5-fold.

8. The method of claim 7, comprising achieving a $C_{tau}$ of elvitegravir that exceeds its $IC_{95}$ by at least 10-fold.

9. The method of claim 1, wherein each cobicistat dose is administered to the patient at a 150 mg dose.

10. The method of claim 1, wherein the rifabutin is administered at a 150 mg dose.

11. The method of claim 1, wherein elvitegravir is administered to the patient at a 150 mg dose.

12. The method of claim 1, wherein the antimycobacterial activity of the rifabutin is increased from the co-administration of the CYP inhibitor.

13. The method of claim 1, wherein the amount of a metabolite of rifabutin, 25-O-desacetylrifabutin, is increased from the co-administration of cobicistat.

* * * * *